US008688209B2

(12) United States Patent
Verbitskiy (10) Patent No.: US 8,688,209 B2
(45) Date of Patent: Apr. 1, 2014

(54) DEVICE FOR AMBULATORY MONITORING OF BRAIN ACTIVITY (75) Inventor: Evgeny Verbitskiy, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 376 days.

(21) Appl. No.: 12/442,558

(22) PCT Filed: Sep. 19, 2007

(86) PCT No.: PCT/IB2007/053801
§ 371 (c)(1),
(2), (4) Date: Mar. 24, 2009

(87) PCT Pub. No.: WO2008/038194
PCT Pub. Date: Apr. 3, 2008

(65) Prior Publication Data
US 2010/0010364 A1    Jan. 14, 2010

Related U.S. Application Data

(60) Provisional application No. 60/826,755, filed on Sep. 25, 2006.

(51) Int. Cl.
*A61B 5/04* (2006.01)
(52) U.S. Cl.
USPC ............ 600/544; 600/382; 600/390; 600/545
(58) Field of Classification Search
USPC .................................. 600/544, 382, 390, 545
See application file for complete search history.

(56) References Cited

U.S. PATENT DOCUMENTS

| 5,222,503 | A  | * | 6/1993  | Ives et al. ...................... 600/544 |
| 6,052,619 | A  |   | 4/2000  | John |
| 6,175,753 | B1 | * | 1/2001  | Menkes et al. ................ 600/386 |
| 2002/0029005 | A1 | * | 3/2002  | Levendowski et al. ....... 600/545 |
| 2002/0188216 | A1 | * | 12/2002 | Kayyali et al. ................ 600/544 |
| 2003/0185408 | A1 | * | 10/2003 | Causevic et al. ............. 381/94.1 |

(Continued)

FOREIGN PATENT DOCUMENTS

| WO | 0249500    A2 | 6/2002 |
| WO | 2006050360 A1 | 5/2006 |

OTHER PUBLICATIONS

Lewicki et al,, "A Review of Methods for Spike Sorting: The Detection and Classification of Neural Action Potentials", Computer Neural Syst. Vol. 9, 1998, p. R53-R78.*

(Continued)

*Primary Examiner* — Christine Matthews
*Assistant Examiner* — Sunita Reddy (57) ABSTRACT

A device for ambulatory monitoring of brain activity includes a patch secured to a head of a monitoring subject and an electrode secured to the head of the monitoring subject. The electrode produces a signal indicating brain activity of the monitoring subject. The device further includes a signal processor that receives the signal produced by the electrode and processes the signal to produce data. The signal processor is secured to the monitoring subject. The device further includes a display that displays the data produced by the signal processor, the display being secured to the monitoring subject. The device also includes a power source secured to the monitoring subject, the power source providing power to the electrode, the signal processor, and the display wherein the monitoring subject may ambulate unimpeded by the patch, the electrode, the signal processor, the display and the power source.

21 Claims, 4 Drawing Sheets

(56) References Cited

U.S. PATENT DOCUMENTS

| | | | |
|---|---|---|---|
| 2003/0204148 A1 | 10/2003 | Lange et al. | |
| 2004/0073127 A1* | 4/2004 | Istvan et al. | 600/513 |
| 2005/0107655 A1* | 5/2005 | Holzner | 600/9 |
| 2005/0240242 A1* | 10/2005 | DiLorenzo | 607/45 |
| 2006/0111644 A1* | 5/2006 | Guttag et al. | 600/544 |

OTHER PUBLICATIONS

Addison, 2005 P.S. Addison, Wavelet transforms and the ECG: a review. Physiol Meas, 26 (2005), pp. R155-R199.*

K. Lehnertz, "Seizure Anticipation Techniques: State of the Art and Future Requirements", Papers from 23rd Annual International Conference of the IEEE Engineering in Medicine and Biology Society, Oct. 25-28, 2001, held in Istanbul, Turkey. pp. 1-4.*

Mormann F, Kreuz T, Andrzejak RG, David P, Lehnertz K, Elger CE, "Epileptic seizures are preceded by a decrease in synchronization", Epilepsy Res. Mar. 2003;53(3):173-185.*

Barreto et al, "Multiresolution Characterization of Interictal Epileptic Spikes Based on a Wavelet Transformation", IEEE, DSPLAB. Eng. FIU, DSP, pp. 193-196, 1995.

Mauro, "EEG Seizure Monitoring" Ambulatory Electroencephalography, E-Medicine, http/:emedicine.medscape.com/artaicle/1137908-overview (htt://www.eMEDICINE.com/neuro/topic445.htm), Oct. 19, 2006.

Kim et al, "Correlation of Interictal Spike-Wave With Thalamic Glucose Metabolism in Juvenile Myoclonic Epilepsy", Neuroreport, vol. 16, No. 11, pp. 1151-1155, 2005.

Ebus et al, "Can Spikes Predict Seizure Frequency? Results of a Pilot Study in Severe Childhood Epilepsies Treated With Vagus Nerve Stimulation", Seizure, vol. 13, No. 7, pp. 494-498, 2004.

Lewicki et al,, "A Review of Methods for Spike Sorting: The Detection and Classification of Neural Action Potentials", Compouter Neural Syst. vol. 9, 1998, pp. R53-R78.

Sarang et al, "A New Epileptic EEG Spike Detection Based on Mathematical Morphology", Proceedings of Biomed, pp. 301-302, 2004.

Lange et al, "Temporo-Spatial Patterns of Pre-Ictal Spike Activity in Human Temporal Lobe Epilepsy", Electroencephalography Clin. Neurophysiol, vol. 56, No. 6, pp. 543-555, 1983.

Waterhouse, "Ambulatory EEG", AmbulatoryEEG: eMEDICINE Clinicla Procedures, http//neuroland.com/sz/eeg/zmbulatory eeg.htm, Updated May 15, 2008.

\* cited by examiner

DEVICE FOR AMBULATORY MONITORING OF BRAIN ACTIVITY

This invention relates generally to devices for monitoring brain activity, such as brain activity in epileptic patients.

Epilepsy is a very common and chronic neurological disorder. Epilepsy is characterized by recurrent and unprovoked seizures. Epileptic seizures are also known as ictal events. The time intervals between seizures in an epileptic neurological patient are known as interictal periods. Approximately 0.8% of the population is affected by epilepsy.

Medication and other therapies that control the intensity of or reduce the frequency of seizures are known. For example, brain stimulation is a known method of controlling and substantially reducing occurrences of seizures in epileptic neurological patients.

Devices for measuring brain activity in order to diagnose and treat neurological disorders such as epilepsy are known. However, such devices are typically extremely cumbersome. For at least these reasons, the measurements obtained by such devices are typically very expensive to obtain. For at least these reasons, the benefit of measuring brain activity from such known devices may be limited to patients able to afford the expense of obtaining such measurements with such devices.

Because known devices for measuring brain activity in neurological patients include prominent protruding wires and boxes, such devices are typically very limiting to the patient. For example, typically, a neurological patient has a somewhat or significantly reduced privacy when being monitored by a known device for measuring the patient's brain activity.

In known devices, it is necessary that an epileptic patient be observed by a neurologist or other medical professional on a regular basis. The observation and assessment of an epileptic neurological patient is performed typically based on two factors. A first factor upon which assessment of an epileptic neurological patient is performed is based on subjective factors. Examples of subjective factors are the patient's self evaluation and the evaluation of the epileptic neurological patient by family members or other persons with whom the epileptic neurological patient has a relationship.

Subjective evaluations of an epileptic neurological patient are often unreliable. For example, a family member of the epileptic neurological patient might not have the necessary medical education to properly evaluate and identify various pertinent aspects of the epileptic neurological patient's behavior.

Examples of more objective ways of assessing and evaluating the behavior of an epileptic neurological patient include the use of an electroencephalogram (hereinafter "EEG"). An EEG is a known method of measuring electrical activity in a human brain by recording data obtained from sensors placed on the scalp. Typically, the sensors are electrodes.

Usually, the devices and methods implemented to obtain EEG measurements are complex. Additionally, obtaining data from an EEG typically requires a trained professional to install and operate the EEG. Further, the analysis of data obtained by an EEG also typically requires a trained medical professional. Thus, an EEG is typically only used for a brief period of time on a given epileptic neurological patient. Furthermore, the sensors and associated hardware used to obtain an EEG are bulky and cumbersome. Such equipment is not suitable for use while an epileptic neurological patient carries on with tasks of everyday life. For example, typically an epileptic neurological patient may not ambulate or otherwise engage in ordinary activities of life while providing readings of brain activity for an EEG.

Some EEG devices exist wherein the epileptic neurological patient may ambulate while data is being obtained. See e.g., Ambulatory Electroencephalography, E-medicine, http://www.emedicine.com/neruo/topic 445.htm; Ambulatory EEG, http://neuroland.com/sz/eeg/ambulatory eeg.htm. However, such devices require a continuous observation of the epileptic medical patient. Likewise, such devices are limited in the length of time they may be employed. For example, known ambulatory EEG devices are typically used for one to three days. Usually, after this limited period of time, known ambulatory EEG devices must be returned to a medical institution or other organization from which the device has been borrowed to obtain measurements from a given epileptic neurological patient.

Because known ambulatory EEG devices are typically used in the manner described above, ambulatory registration of EEG is typically used only rarely for any given epileptic neurological patient. Thus, the majority of data available to a neurologist when evaluating a given epileptic neurological patient is typically almost entirely subjective in nature.

During interictal periods, one can observe abnormal brain discharges that are associated with epilepsy. These abnormal brain discharges are often referred to as spikes. Epileptic spikes are interictal events (i.e., occurring between epileptic seizures). Epileptic spikes are transient brain discharges that are clearly distinguishable from background brain activity.

A typical epileptic spike has a peak that is at least somewhat pronounced and pointed, typically followed by a valley that is also usually somewhat pronounced and pointed. The magnitude of the peaks and valleys of epileptic spikes clearly distinguish that brain activity from other ordinary levels of brain activity. Typically an epileptic spike has a duration in the range of 20 to 70 msec. However, both the magnitude and the duration of an epileptic spike can vary.

In other words, an epileptic spike corresponds to the synchronized activity of a number of brain neurons having a particular volume. An epileptic spike could be understood as a miniature epileptic seizure event that fails to develop into a full clinical epileptic seizure in the epileptic neurological patient. Nevertheless, this activity is an undesirable brain activity. Sometimes, the observation of epileptic spikes is the only evidence of the presence of epilepsy in an epileptic neurological patient. For example, some patients respond well to anti-epileptic drugs. In such patients, the occurrence of epileptic seizures is very infrequent. Nevertheless, such patients typically regularly display spikes in observations of their brain discharges.

Interictal spikes in the brain discharges of epileptic neurological patients have been studied, and continue to be studied, extensively. For example, it has been observed by some practitioners that the frequency of epileptic spikes has little correlation with the onset of a next epileptic seizure in an epileptic neurological patient. Thus, according to some practitioners, the presence of spikes and a count of spikes in the brain discharges of an epileptic neurological patient are of little value. However, other practitioners believe that the observation of spikes in the brain discharges of an epileptic neurological patient have considerable value. Such practitioners believe that the presence, frequency and characteristics of epileptic spikes in a given epileptic neurological patient include information about the state of that patient's epilepsy in general that is useful to a neurologist treating the epileptic neurological patient. See, e.g., S C Ebus et al., *Can spikes predict seizure frequency? Results of a pilot study in severe childhood epilepsies treated with vagus nerve stimulation*, Seizure 13(7): 494-8 (2004); J H Kim et al., *Correlation of*

*interictal spike-wave with thalamic glucose metabolism in juvenile myoclonic epilepsy*, Neuroreport 16(11): 1151-1155 (2005).

For certain types of epilepsy some evidence indicates that a clear correlation exists between the power or intensity of the spike observed in an epileptic neurological patient and the ability to predict accurately the oncoming occurrence of an epileptic seizure. See, e.g., H H Lange et al., *Temporo-spatial patterns of pre-ictal spike activity in human temporal lobe epilepsy*, Electroencephalography Clin Neurophysiol, 56(6): 543-55 (1983). For example, temporal lobe epilepsy (TLE) is the most frequent of epilepsy experienced by epileptical neurological patients. Research has shown that power of spike observations in epileptic neurological patients has a predictive correlation to the occurrence of epileptic seizures experienced by TLE patients.

Although it is not currently clear the predictive benefit of measuring frequency or intensity of spikes measured in epileptic neurological patients, it remains clear that the observation and measurements of such spikes are featured prominently in predictive research.

Typically, the drugs administered to an epileptic neurological patient in an attempt to reduce the intensity and frequency of epileptic seizures experienced by that patient need to be varied. For example, most anti-epileptic drugs include negative side effects. Thus, one reason why anti-epileptic drugs are typically varied is to reduce the intensity of unwanted side effects experienced by the epileptic neurological patient as a result of taking a given anti-epileptic drug. The need for information regarding brain activity in the epileptic neurological patient is increased as a result of the necessity of regularly varying an epileptic neurological patient's anti-epilepsy drug regimen. As described above, the ambulatory registration of EEG is a complex task, both from a technical point of view involving cumbersome devices and cumbersome placement of electrodes on the scalp of an epileptic neurological patient, and also in view of the later analysis of the data recorded by the device by trained laboratory personnel or a clinical neurologist. Thus, as described above, the ambulatory registration of EEG is not performed very often on a given epileptic neurological patient.

For at least the foregoing reasons, a need exists for a simplified device for obtaining EEG data in an epileptic neurological patient.

Similarly, the need exists for a small device for obtaining EEG data from an epileptic neurological patient.

Likewise, a need exists for a portable device for obtaining EEG data from an epileptic neurological patient.

Similarly, there is a need for a device that obtains EEG data from an epileptic neurological patient without encumbering the mobility of the patient.

Likewise, there is a need for a device that obtains EEG data from an epileptic neurological patient without impeding the lifestyle of the patient.

Similarly, there is a need for a device that obtains EEG data from an epileptic neurological patient without requiring constant observation of the patient while obtaining the EEG data.

Further, there is a need for a device that obtains EEG data from an epileptic neurological patient while operating for a long period of time between analyses of data collected by the device.

In summary, there is a need for a device that obtains EEG data from an epileptic neurological patient that can be operated by the patient without additional supervision by another person.

The foregoing objects and advantages of the invention are illustrative of those that can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variation which may be apparent to those skilled in the art. Accordingly, the present invention resides in the novel methods, arrangements, combinations and improvements herein shown and described.

In light of the present need for a device as described above, a brief summary of various exemplary embodiments is presented. Some simplifications and omission may be made in the following summary, which is intended to highlight and introduce some aspects of various exemplary embodiments, but not to limit the scope of the invention. Detailed descriptions of a preferred exemplary embodiment adequate to allow those of ordinary skill in the art to make and use the invention concepts will follow in later sections.

In various exemplary embodiments, a device for ambulatory monitoring of brain activity is implemented in a target group. In various exemplary embodiments, the target group is composed of epileptic neurological patients experiencing localized epilepsy. In various exemplary embodiments, a device for ambulatory monitoring of brain activity includes an electrode located in proximity to a source of localized epileptic activity in an epileptic neurological patient. In various exemplary embodiments, a device for ambulatory monitoring of brain activity detects spikes at a source of localized epileptic activity in an epileptic neurological patient.

In various exemplary embodiments, a stand alone device is provided that counts the epileptic spikes observed during a period where data is measured by the device. In various exemplary embodiments, measurements of spike activity are obtained daily and weekly for use by epileptic neurological patients and for use by the doctors and other medical professionals assessing the state of health of an epileptic neurological patient. This data is also used in various exemplary embodiments to select the most effective medication for an epileptic neurological patient, and to adjust the most beneficial level of medication for an epileptic neurological patient. In various exemplary embodiments, a device is provided that may be used by an epileptic neurological patient to obtain EEG measurements in the privacy of the patient's home and at a time most convenient to the patient.

In various exemplary embodiments, the device includes a microprocessor chip. In various exemplary embodiments, the microprocessor chip is programmed to operate an algorithm on the data obtained by the sensors of the device. In various exemplary embodiments contemplated for application in the future, the algorithm incorporates predictive factors subsequently determined to be correlated between measurements of spikes in epileptic neurological patients and the oncoming occurrence of an epileptic seizure.

In various exemplary embodiments, EEG data is analyzed by the device. In various exemplary embodiments, no further transfer of data or analysis by a person other than the epileptic neurological patient is required.

In order to better understand the present invention, reference is made to the accompanying drawings, wherein.

Referring now to the drawings, in which like numerals refer to like components or steps, there are disclosed broad aspects of preferred embodiments.

Figure 1:
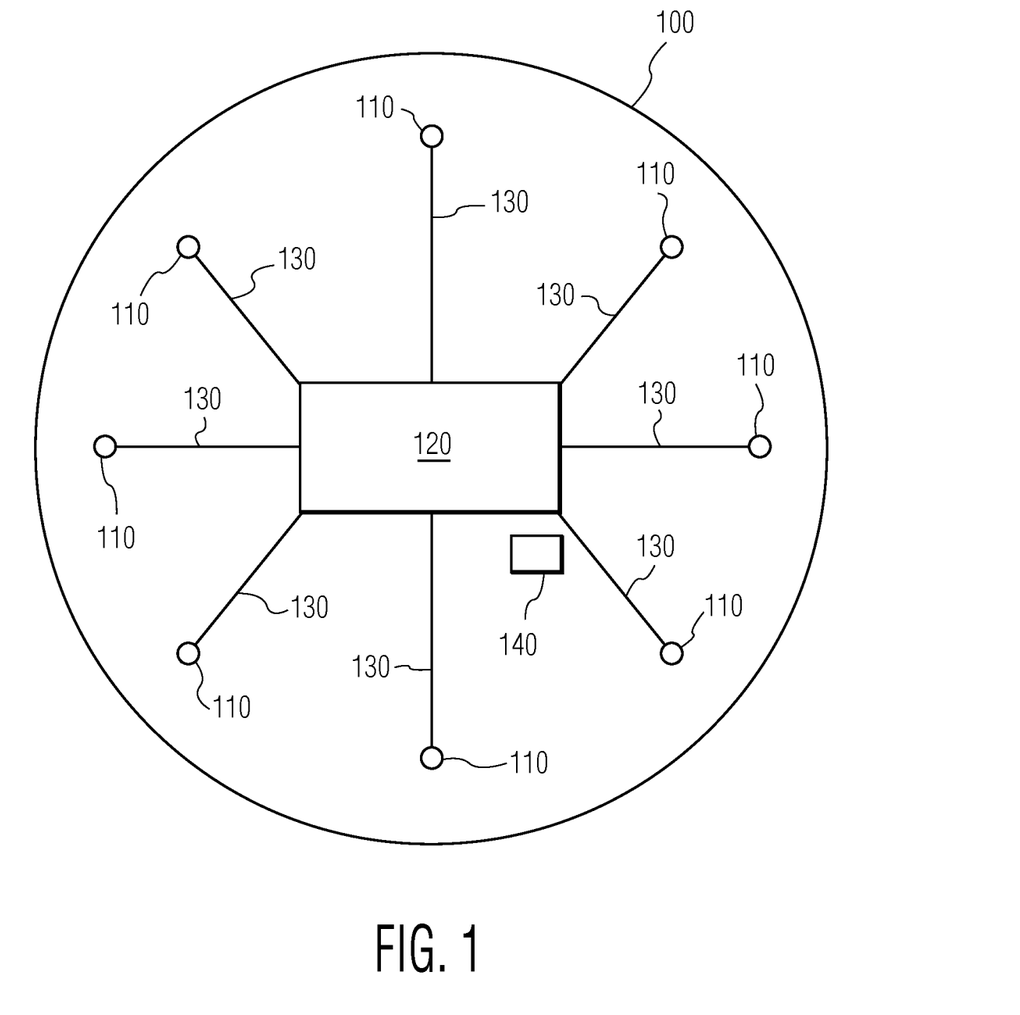
FIG. 1 is a schematic of an exemplary device for ambulatory monitoring of brain activity according to the present invention.

FIG. 1 is an exemplary embodiment of a device 100 for ambulatory monitoring of brain activity. The exemplary device 100 includes a number of exemplary electrodes 110, a power source such as a battery (not shown), and a signal processor 120 for processing data received by the device. The device 100 may be fabricated as a patch or a strap to be worn on an epileptic neurological patient. The signal processor and the power source may also be incorporated into the exemplary patch or strap of the device 100.

An array of electrodes 110 are arranged around a signal processor 120 and connected to the signal processor 120 by integral wires 130. If integrated with a patch or strap, the integral wires 130 are preferably fully contained within the patch or strap of the device 100. Thus, the integral wires 130 are not external to the patch or strap of the device 100.

Electrode signals are received from the electrodes 110 and amplified and digitized by the signal processor 120.

Each of the electrodes 110 obtains its own individual measurement of a brainwave signal. Thus, each individual electrode 110 generates a signal from which an epileptic spike can be individually identified in the EEG signal.

The signal processor 120 is capable of analyzing each signal from each individual electrode 110 separately or a plurality of signals from a plurality of electrodes 110 together. The signal processor 120 is also capable of analyzing all signals obtained from all of the plurality of electrodes 110 together.

It may be preferable to combine signals from more than one electrode in order to obtain the most beneficial information for analysis by the signal processor 120 for each individual epileptic neurological patient, and for each separately identifiable class of epileptic neurological patients.

As described above, epileptic spikes of brain discharges have a very unique and distinguishable shape. The signal processor 120 includes a filter that is used to identify epileptic spikes of brain discharges by identifying the unique shape of such spikes.

The filter is implementable in the time domain, in the frequency domain, or in the signal processor 120 and based on wavelet coefficients. A plurality of filters are implementable in the exemplary digital processor 120 including two or more of a time domain filter, a frequency domain filter, and a filter based on wavelet coefficients.

The signals obtained from the electrodes 110 by the signal processor 120 are convertable from the time domain to the frequency domain and from the frequency domain to the time domain. Also, a matched filter may be optionally implemented for analyzing the signals obtained from the electrodes 110 by the signal processor 120 in both the frequency domain and the time domain.

The EEG signal obtained from one or more of the electrodes 110 by the signal processor 120 may be convolved using a particular filter. The results of convolving any EEG signal with a filter may be compared to a predetermined threshold. The presence of a spike may be determined when the convolved EEG signal is above a predetermined threshold.

The approach described above is implementable with wavelets. Thus, a choice is made regarding an appropriate wavelet. Wavelet decomposition may be performed. Coefficients may be determined from the wavelet decomposition and compared to a predetermined threshold. The presence of a spike is determined when coefficients obtained from wavelet decomposition exceed a predetermined threshold.

Where the presence of a spike is determined by combining the analysis of multiple signals obtained from multiple electrodes 110, one or more of the forms of analysis described above may be simultaneously performed on a plurality of signals. The presence of a spike is only identified when all of the signals analyzed simultaneously indicate the presence of a spike. In this manner, brain activity that is more localized and resulting in an identification of a spike at a small subset of electrodes 110 will not be identified as an actual epileptic neurological spike activity because it was not detected at other electrodes 110. Disclosure pertinent to certain aspects of this methodology can be found in Barreto et al., *Multiresolution Characterization of Interictal Epileptic Spikes Based on a Wavelet Transformation*, http://dsplab.eng.fiu.edu/DSP/Research/Research 002.htm; R. Sarang, et al., *A New Epileptic EEG Spike Detection Based on Mathematical Morphology*, Proceedings of BioMED 2004.

The digital processor 120 optionally includes a counter. The counter increases its increment by one whole number each time a spike is detected by the processor 120 based on the signals received from the electrodes 110. Thus, the device 100 operates in a manner somewhat analogous to a Geiger counter, counting the number of spikes detected, and using the count of the number of spikes detected to determine a level of epileptic activity within the brain of the epileptic neurological patient upon which the device 100 is implemented.

The information obtained by the processor 120 from the electrodes 110 is also capable of being analyzed based on an intensity of the number of spikes occurring in a given time period. For example, the number of spikes identified per hour is counted. A critical threshold is set at a predicted number of spikes per hour for alarming. Thus, an alarm is triggered when the intensity of the number of spikes identified in a given time period exceeds a predetermined critical alarm value.

The presence of spikes is identifiable in clusters. A cluster of spikes is a group of spikes that occur together within a predetermined amount of time followed and preceded by a greater period of time when no spike is measured.

The analysis of the information obtained by the processor 120 from the electrodes 110 may include an analysis of clusters. A predetermined threshold exists for a number of clusters occurring in a given period of time. An alarm is triggered when the number of clusters measured in a given period of time exceeds a predetermined threshold. A predetermined threshold for clusters represents either a minimum threshold or a maximum threshold.

The threshold may optionally pertain to the length of time of a cluster. Thus, an alarm may be triggered if the length of a given cluster is too long or if the length of a cluster is too short.

Some epileptic neurological medical practitioners believe that spike activity in the brain waves of the epileptic neurological patient drops preceding the occurrence of an epileptic neurological seizure event. Thus, identifying the absence of, or a reduction in the frequency of occurrence of, clusters is believed to be beneficial information for predicting the future or imminent occurrence of an epileptic neurological seizure in an epileptic neurological patient.

Thus, many epileptic neurological medical practitioners believe that the imminent future occurrence of an epileptic neurological seizure event in an epileptic neurological patient can be predicted with much greater accuracy based on an analysis of spike data according to one or more of the various exemplary embodiments described above and below. Although it is not currently known how to predict the onset of an epileptic neurological seizure with a great degree of accuracy in time, it is believed that an advance warning can be given to an epileptic neurological patient of the likelihood of a seizure occurring in an upcoming period of time such as a twenty-four hour or a forty-eight hour time interval. It should be apparent that, as the understanding of the relationship between spikes and epileptic neurological seizures advances in the future, the various exemplary embodiments described herein can be modified to implement that future developed analysis of information.

Optionally, the processor 120 further includes a light emitting diode (LED) display. In an embodiment including the counter function in the digital processor 120 and an LED display, the LED display displays the number of spikes observed, identified and counted.

The device 100 further optionally includes a port 140 used to connect the digital processor 120 to a computer, a personal data assistant (PDA), or some other external data processing device. Data received and/or processed by the digital processor 120 is transmitted to an external device via the exemplary port 140.

The data may be transferred from the digital processor 120 to an external device via the exemplary port 140 at the end of a predetermined measurement period or even in the middle of a predetermined measurement period.

Information regarding each individual spike may be optionally more involved than simply counting the occurrence of the spike. For example, the intensity of the spike may be recorded by the digital processor 120.

The length of time from beginning to end of each spike may be recorded by the exemplary digital processor 120. Both the length of time and the intensity of each spike may be recorded by the digital processor 120. Thus, in some advanced exemplary embodiments, a graph is created that plots the intensity of a spike against time as each spike occurs based on data gathered by the exemplary digital processor 120. This more advanced storage of data by the digital processor allows increased detail in the scrutiny by a medical professional of the spike occurrence in the patient upon which the exemplary device 100 is implemented.

Figure 2:
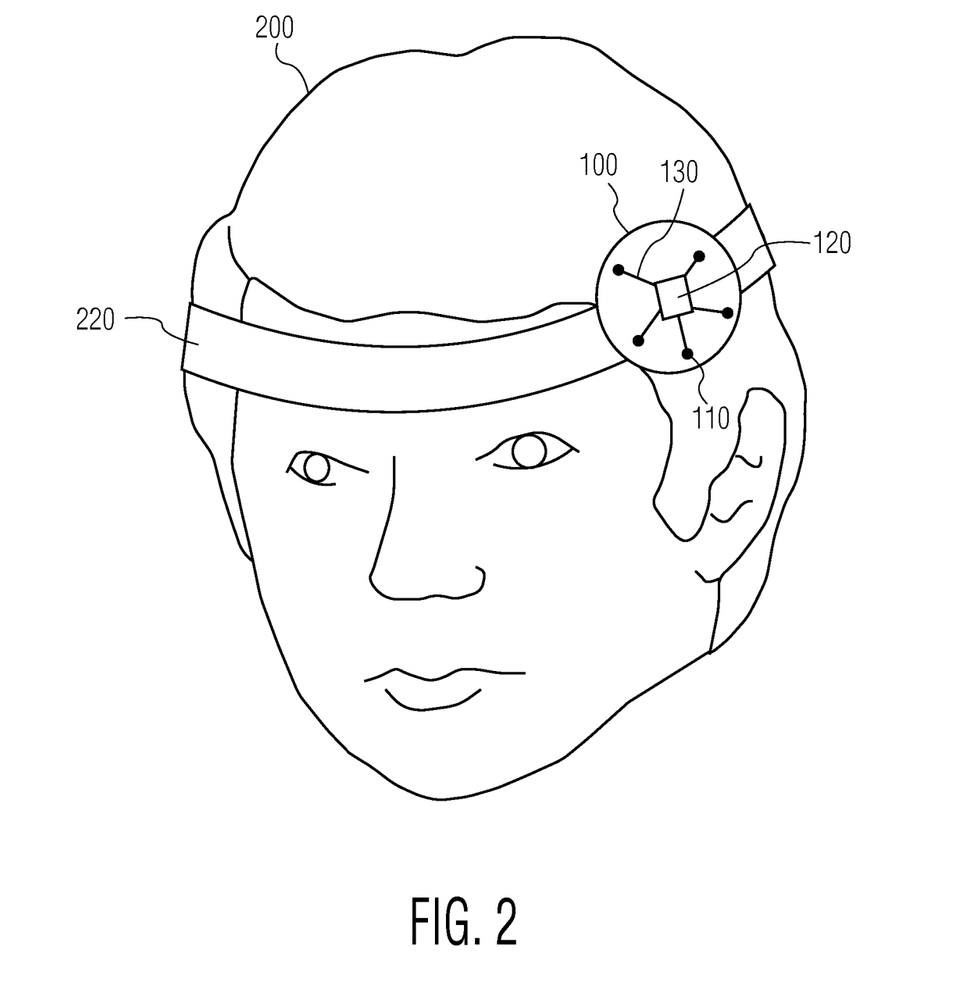
FIG. 2 is a perspective view of an exemplary implementation of an exemplary device for ambulatory monitoring of brain activity according to the present invention.

FIG. 2 is a perspective view of the exemplary device 100 for ambulatory monitoring of brain activity installed on the head of the exemplary epileptic patient 200. In this exemplary embodiment, the exemplary device 100 is attached to the head of the epileptic neurological patient 200 by a strap 220 that wraps horizontally the head of the exemplary epileptic neurological patient 200. Thus, in various exemplary embodiments, a strap 220 is included as an integral part of the device 100. Similarly, in various exemplary embodiments, the sensors 110 and integral wires 130 extend along the exemplary strap 220 beyond the portion of the device 100 including the processor 120.

Figure 3:
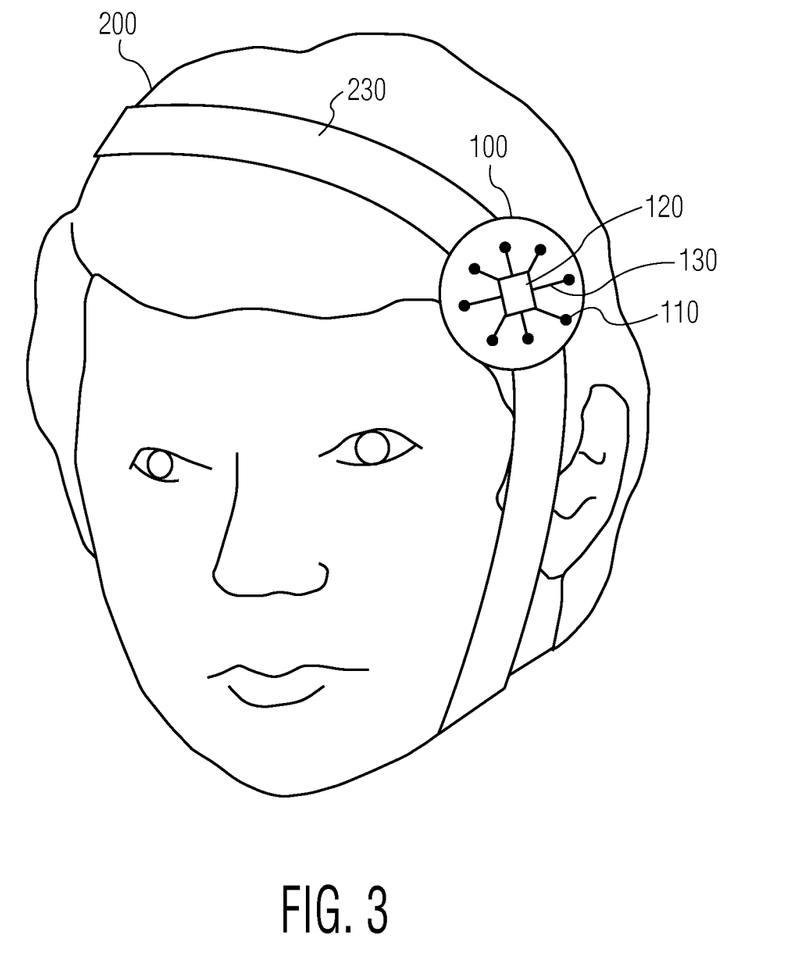
FIG. 3 is a perspective view of a second exemplary embodiment of an implementation of an exemplary device for ambulatory monitoring of brain activity according to the present invention.

FIG. 3 is a perspective view of a second exemplary embodiment of the exemplary device 100 for ambulatory monitoring of brain activity installed on the head of an exemplary epileptic neurological patient 200. In this embodiment, the exemplary device 100 for ambulatory monitoring of brain activity is installed on the head of the epileptic neurological patient 200 by an exemplary strap 230 that passes horizontally around the head of the epileptic patient 200. The strap 230 optionally passes underneath the chin of the epileptic patient 200. As in the exemplary embodiment shown in FIG. 2, in various exemplary embodiments of the strap 230, the sensors 110 and integral wires 130 are arrayed along the strap 230 next to portions of the patient's head 200 beyond the portion of the exemplary device 100 that includes the signal processor 120.

Figure 4:
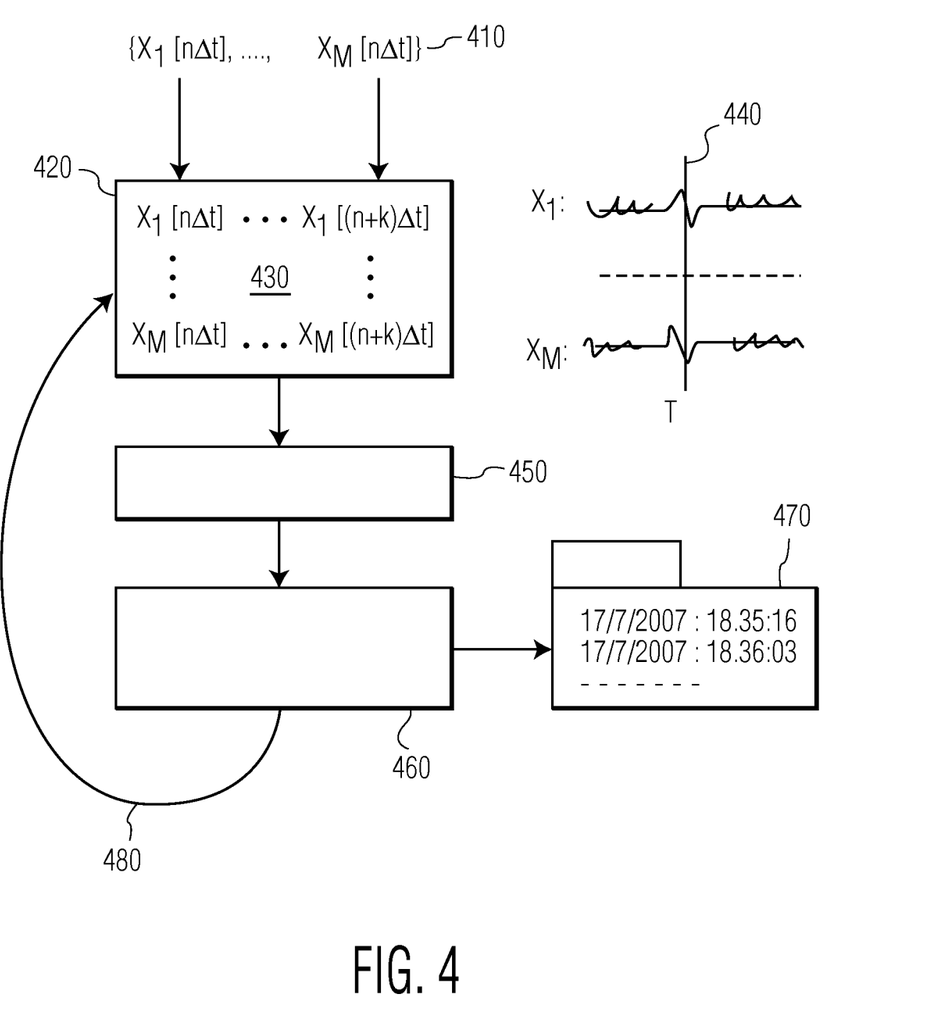
FIG. 4 is a block diagram flowchart of an exemplary embodiment of a method for identifying a spike in an epileptic neurological patient according to the present invention.

FIG. 4 is a block diagram flowchart of an exemplary embodiment of a method for identifying a spike in an epileptic neurological patient according to the present invention. First, an input or a plurality of inputs are made to a buffer in step 410. Each input in step 410 represents a signal obtained from one of the sensors 110. The buffer 420 is a component of the signal processor 120. The buffer 420 is not physically contained in the same physical space as the signal processor 120.

Next, in step 430, a matrix is constructed containing, in each line, each signal received from the inputs in step 410, and a plurality of rows of lines representing the measurements of the signals obtained in step 410 as time progresses. Thus, in step 440, a wave pattern is constructed from the signals input in step 410 and from the matrix constructed in step 430.

Next, the data obtained and processed in steps 410, 430 and 440, is analyzed. The analysis performed in step 450 includes the identification and detection of the presence or absence of one or more epileptic neurological spikes.

In exemplary step 460, the time at which an epileptic neurological spike was detected is recorded and saved in the signal processor 120. Thus, in exemplary step 470, a table is constructed listing the date and time of each epileptic neurological spike identified and detected. After the conclusion of the previously described exemplary steps, the buffer is updated in step 480.

Although preferred embodiments have been described in detail, it should be understood that these preferred embodiments are not an exhaustive list of embodiments, and the details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed is:

1. A device for ambulatory monitoring of brain activity, comprising:
   a plurality of electrodes adapted to be operatively secured to a head of a monitoring subject, each electrode producing a signal indicating brain activity of the monitoring subject;
   a signal processor that receives the signals produced by the plurality of electrodes and processes the signals to produce data, the signal processor adapted to be secured to the monitoring subject and analyzing the signals such that the signal processor determines an occurrence of a brain spike based on a) a convolved signal that exceeds a first fixed threshold and b) coefficients determined from wavelet decomposition that exceed a second fixed threshold;
   a display that displays the data produced by the signal processor, the display adapted to be secured to the monitoring subject; and
   a power source adapted to be secured to the monitoring subject, the power source providing power to the plurality of electrodes, the signal processor, and the display,
   wherein the monitoring subject may ambulate unimpeded by the plurality of electrodes, the signal processor, the display and the power source.

2. The device according to claim 1, further comprising a communication port for transferring the data to a remote device.

3. The device according to claim 1, further comprising a strap adapted to be disposed around the head of the monitoring subject.

4. The device according to claim 3, wherein the plurality of electrodes are integral to the strap.

5. The device according to claim 1, further comprising a patch adapted to be attached to the head of the monitoring subject, wherein the plurality of electrodes are integral to the patch.

6. A method of ambulatory monitoring of brain activity, comprising:
   operatively securing a plurality of electrodes to the head of the monitoring subject;
   securing a signal processor to the monitoring subject;
   securing a display to the monitoring subject;
   securing a power source to the monitoring subject;
   providing power from the power source to the plurality of electrodes, the signal processor, and the display;
   producing signals indicating brain activity of the monitoring subject;
   transmitting the signals from the plurality of electrodes to the signal processor;
   analyzing the signals to determine a period of time when an absence or reduction in the number of neural spikes is measured to determine whether a neurological seizure event is imminent,
   producing data based on the period of time;
   displaying the data on the display, wherein the monitoring subject may ambulate unimpeded by the plurality of electrodes, the signal processor, the display and the power source.

7. The method according to claim 6, further comprising transferring the data from a communications port to a remote device.

8. The method according to claim 7, further comprising securing a strap around the head of the monitoring subject.

9. The method according to claim 8, wherein the plurality of electrodes are integral to the strap.

10. The method according to claim 6, wherein analyzing includes implementing a filter in the time domain.

11. The method according to claim 6, wherein analyzing includes implementing a filter in the frequency domain.

12. The method according to claim 6, wherein analyzing includes implementing a filter based on a wavelet coefficient.

13. The method according to claim 6, wherein analyzing includes implementing a matched filter in the frequency domain and the time domain.

14. The method according to claim 6, wherein analyzing includes convolving the signals.

15. The method according to claim 6, wherein analyzing includes comparing a value to a predetermined threshold.

16. The method according to claim 6, wherein analyzing includes analyzing the signals from the plurality of electrodes and identifying the occurrence of brain spike only if the brain spike is indicated as being present based on the analysis of each of the signals.

17. The method according to claim 6, wherein analyzing includes counting a number of brain spikes.

18. The method according to claim 6, wherein analyzing includes analyzing clusters of brain spikes.

19. The method according to claim 6, wherein analyzing includes analyzing the signals as a function of time.

20. The method according to claim 6, further comprising issuing an alarm when a result of the analysis satisfies a predetermined alarm condition.

21. A method of ambulatory monitoring of brain activity, comprising:
   providing power from a power source secured to a monitoring subject to a plurality of electrodes operatively secured to a head of the monitoring subject, a signal processor secured to the monitoring subject, and a display secured to the monitoring subject;
   producing signals indicating brain activity of the monitoring subject;
   transmitting the signals from the plurality of electrodes to the signal processor;
   analyzing the signals to determine a period of time when an absence or reduction in the number of neural spikes is measured to determine whether a neurological seizure event is imminent,
   producing data based on the period of time;
   displaying the data on the display, wherein the monitoring subject may ambulate unimpeded by the plurality of electrodes, the signal processor, the display and the power source.

* * * * *